US 9,241,826 B1
Jan. 26, 2016

(12) United States Patent
Shih

(54) TOPICAL WOUND HEALING DEVICE FOR DYNAMIC ELASTIC INJURY SITE

(71) Applicant: Lih-Bin Shih, San Diego, CA (US)

(72) Inventor: Lih-Bin Shih, San Diego, CA (US)

( * ) Notice: Subject to any disclaimer, the term of this patent is extended or adjusted under 35 U.S.C. 154(b) by 364 days.

(21) Appl. No.: 13/761,843

(22) Filed: Feb. 7, 2013

Related U.S. Application Data

(60) Provisional application No. 61/633,263, filed on Feb. 8, 2012.

(51) Int. Cl.
*A61F 7/02* (2006.01)
*A61B 17/132* (2006.01)
*A61M 35/00* (2006.01)

(52) U.S. Cl.
CPC .............. *A61F 7/02* (2013.01); *A61B 17/132* (2013.01); *A61M 35/00* (2013.01)

(58) Field of Classification Search
CPC ........... A61B 2018/00005; A61B 2018/00011; A61B 2018/00023; A61B 2018/00047; A61B 2018/00059; A61B 2018/00089; A61B 2018/00095; A61B 2018/00101; A61B 17/132; A61B 13/1322; A61B 17/1325; A61B 17/0057; A61B 17/1327; A61F 5/32; A61F 2007/0228; A61F 2007/0203; A61F 2007/0209; A61F 2007/0222; A61F 2007/0244; A61F 2007/0247; A61F 2007/0252; A61F 2007/0261; A61F 2007/0271; A61F 2007/0269; A61F 2007/0282; A61F 2007/0295; A61F 2007/126; A61F 2007/0035; A61F 2007/0292; A61F 7/12; A61F 7/0085; A61F 7/02; A61F 13/00029; A61F 13/00038; A61F 13/00063; A61F 2013/00089; A61F 2013/00119; A61F 2013/00191; A61F 2013/00174; A61F 2013/00178; A61F 2013/002; A61M 2025/028; A61L 26/00
See application file for complete search history.

(56) References Cited

U.S. PATENT DOCUMENTS

| | | | |
|---|---|---|---|
| 4,557,262 A | 12/1985 | Snow | |
| 5,728,120 A | 3/1998 | Shani et al. | |
| 6,647,986 B1 | 11/2003 | Korotko et al. | |
| 2004/0039413 A1 | 2/2004 | Akerfeldt et al. | |
| 2004/0133251 A1* | 7/2004 | Altshuler et al. | ............... 607/88 |
| 2005/0080368 A1* | 4/2005 | Hurwitz | ............... 602/2 |
| 2005/0113866 A1 | 5/2005 | Heinz et al. | |
| 2006/0058841 A1 | 3/2006 | Mills et al. | |
| 2007/0239092 A1 | 10/2007 | Ross et al. | |
| 2009/0281565 A1 | 11/2009 | McNeese et al. | |

(Continued)

OTHER PUBLICATIONS

Dauerman HL et al. Vascular Closure Devices, The Second Decade, JACC 2007;50(17):1617-1626.

(Continued)

*Primary Examiner* — Jocelin Tanner

(57) ABSTRACT

This invention discloses a topical cooling compressive hemostasis and wound healing device and methods thereof for affecting a percutaneous access wound or an acute surgical wound where the device is compatible with physiological, circulatory and cellular microenvironments of the injury and conforming to the injury site anatomy. The device promotes hemostasis, sustains hemostasis and improves wound healing quality by controlling and affecting vasculature motions of the injury site during various wound healing phases. The device incorporates an elastic material compatible with the elastic nature of the injured vessel to promote comfort and safety. The elastic material is further thermally conductive to deliver and transport cooling and a therapeutic agent to the wound site. The device further incorporates an anatomically conforming lateral stabilization component to stabilize the injury sits and its surroundings.

17 Claims, 8 Drawing Sheets

(56) References Cited

U.S. PATENT DOCUMENTS

2010/0280541 A1    11/2010    Lampropoulos et al.
2011/0196417 A1    8/2011    Clark et al.

OTHER PUBLICATIONS

Aalkjaer C et al. Vasomotion: Cellular Background for the Oscillator and for the Synchronization of Smooth Muscle Cells. Br J Pharmacol, 2005; 144(5):605-616.

King NA at al. A Randomized Controlled Trial Assessing the Use of Compression versus Vasoconstriction in the Treatment of Femoral Hematoma Occurring after Percutaneous Coronary Interventions. Heart and Lung, 2008;37:205-210.

Achneck HE at al. A Comprehensive Review of Topical Hemostatic Agents. Ann Surg 2010, 251:217-228.

Sakurai T at al. Effects of sympathetically induced vasomotion on tissue-capillary fluid exchange. Am. J. Physiol. Heart Circ Physiol 2006;291: H1761-H1767.

* cited by examiner

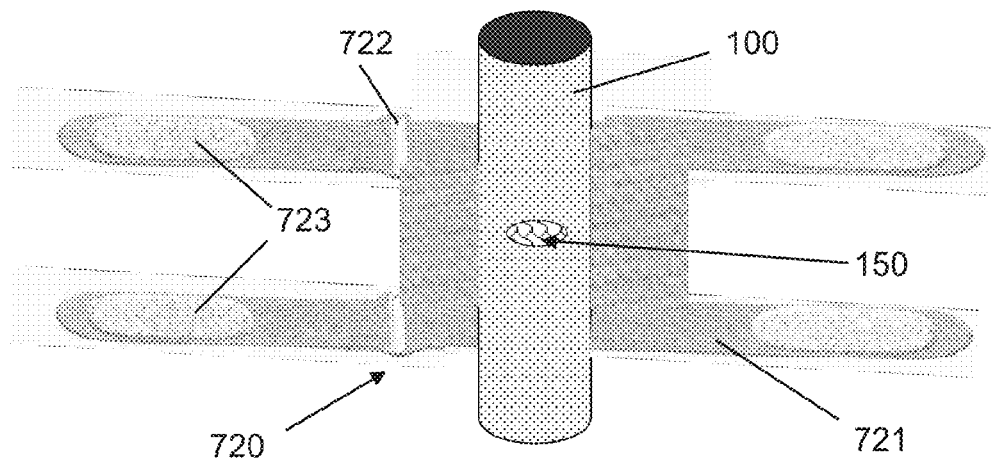
FIG. 7A
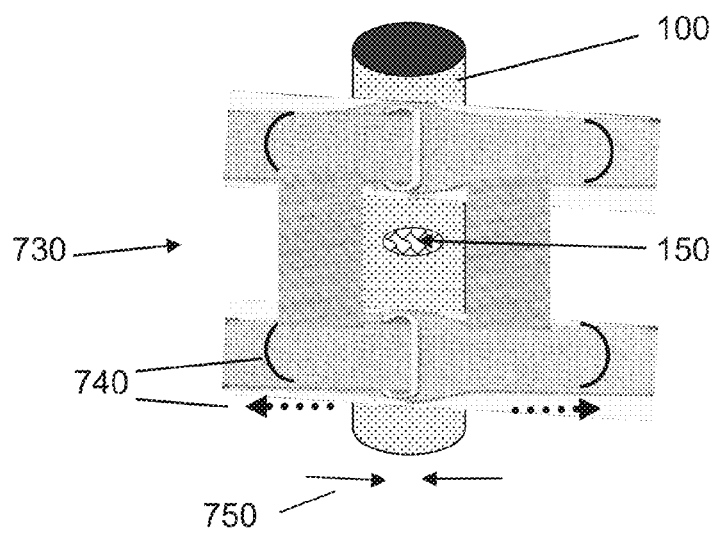
FIG. 7B
FIG. 7

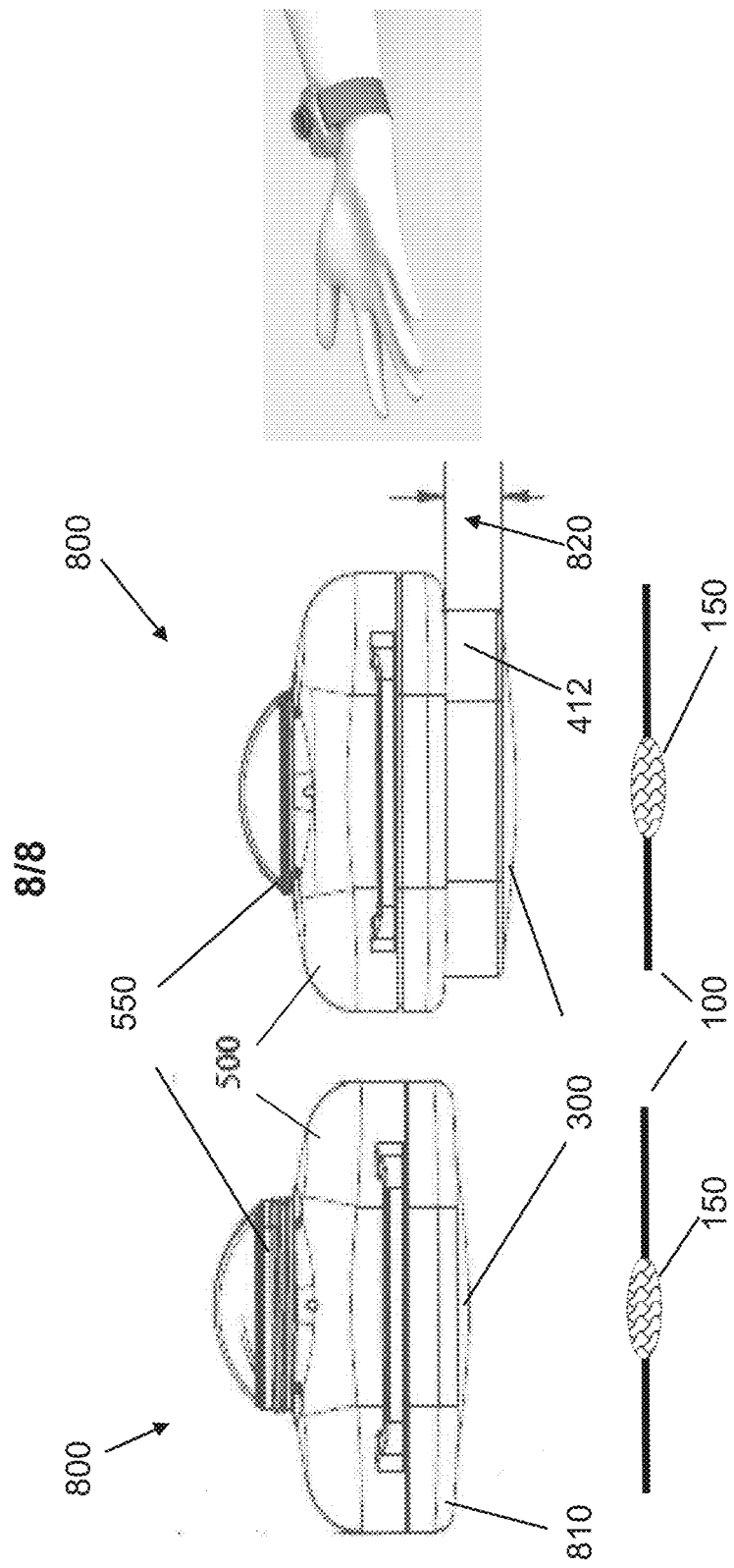

TOPICAL WOUND HEALING DEVICE FOR DYNAMIC ELASTIC INJURY SITE

CROSS-REFERENCE TO RELATED APPLICATION

This application claims priority to U.S. Provisional Application No. 61/633,263, filed on Feb. 8, 2012, which is incorporated herein by reference in its entirety.

BACKGROUND OF THE INVENTION

Human physiological signals are perpetual. These signals are spontaneous or induced with molecular, cellular, neural and/or electrical origins. Many of these physiological signals manifest themselves in motions and movements in order to perform biologic and biochemical functions that sustain life. The better known motions are heartbeats, respiration and cardiopulmonary functions. But there are far subtler motions in all parts of a human body necessary and essential to support life. These physiological motions have been shown to follow certain non-linear dynamic laws, and possess fractal features and entrainment properties. These physiological motions are related to demographic factors, such as gender and age, and closely associated with the health or disease conditions of a human body. Physiological dynamics, while not always seen or felt by humans, are nonetheless always present and essential to life.

In particular, these constant physiological motions are present in the entire cardiovascular and circulatory system including arteries, veins and capillaries. Vasculature motions include vasomotion, vasodilation, vasoconstriction and vasospasm. These spontaneous motions in the vasculature system also lead to rhythmic changes in vessel diameter, wall thickness and vessel distensibility. Furthermore, blood vessels are elastic and characterized by certain viscoelastic properties. The dynamic and elastic nature of the vessels has particular effects on the success or failure of a therapeutic cardiovascular device.

Percutaneous access for various cardiovascular interventions is considered a safer and less invasive alternative to surgeries. This procedure has been developed since early 1950 and has now evolved into a popular and useful procedure treating a wide range of cardiovascular and vascular diseases including abdominal aortic aneurysm and heart valve repairs. Percutaneous access is either diagnostic or interventional (e.g. percutaneous coronary intervention, or PCI) with several possible access sites including artery, vein, femoral, radial or brachial locations. Each access site has its own advantages and limitations. The choice of the access site is often dependent on the disease condition, and on the preference of the practicing interventional cardiologist or radiologist. In all of these percutaneous interventions, there is a common denominator, i.e. hemostasis and healing of the vascular access site wound.

The preference in access site of a medical patient is geographically stratified and has evolved over time. Today, the angioplasty PCI procedure in the US is >95% femoral access while the radial access is favored in Europe and Asia at >70%. In the US, there has been a surge of radial access since 2007, mainly in response to the unabated bleeding and medical complications associated with femoral access. Reducing access site bleeding complications is the main reason cited for the conversion to radial access, even though radial access has its own limitations and disadvantages. Access site hemostasis and subsequent wound healing is important by itself as bleeding complications are often associated with serious human and economical costs; it is also important because it either contributes to the success of, or compromises, the underlying intervention.

Traditional design of hemostasis devices for percutaneous access site is based on a mechanistic barrier concept treating the "hole" of the injured vessel more like a hole in a leaking water pipe, i.e. treating the injured vessel as a stationary and motionless structure with constant dimensions. This barrier concept is reflected by many conventional terms such as "seal", "plug", or "clamping". As such, current implant hemostasis devices provide a physical barrier to "plug" or "seal" the vascular "hole", while current topical hemostasis devices provide a mechanical barrier to "clamp" the injured vessel from outward blood flow, and both as means of causing hemostasis. In reality, these actions only provide a resistive force to resist blood from gushing out after catheter removal, they do not cause hemostasis as defined by a cascade of time-dependent cellular processes of platelet aggregation, fibrin formation and subsequent wound healing. Furthermore, blood vessels are not a rigid stationary structure. Instead, blood vessels are soft, elastic and in various motions with constant changes in vessel diameter, wall thickness, and tone.

Because of the significant conceptual discrepancies, access site bleeding complications remain unabated after more than half a century. While the percutaneous technique has made significant advances, i.e. expanding to treating different types of diseases, increasing the size of the catheter and the aggressive use of anticoagulants, manual compression remains today as the "gold standard" in hemostasis management. Clinical experience and large scale statistics have amply validated that manual compression is inadequate and inapplicable in many situations and that the access site bleeding and vascular complications remain a significant medical and economic issue decades after the advent of the percutaneous procedure.

There are two types of topical hemostasis devices currently on the market addressing the percutaneous access site. One is the "topical patch" where a manufacturer claims to stop bleeding faster by visually judging no blood oozing out on the skin puncture surface. The other is the equivalent of manual compression, i.e. providing a compression force with a mechanical device or an instrument. The former (topical patch) provides a false sense of hemostasis as the injury site is under the skin on a breached vessel, and skin surface hemostasis is not an indication of the hemostasis of the injured vessel. Nor does the latter (manual or device compression) solve the problem. In fact, an exhaustive scientific literature search has shown that compression pressure does not cause platelet aggregation and fibrin formation. Not only does compression not promote the cellular processes of coagulation, the practice of strong and prolonged compression hinders cellular coagulation and causes additional injury and neurological damage to the patient. It is well documented that the initial seemingly successful hemostasis on the skin surface can turn into a serious bleeding medical event later in an unpredictable way. The unpredictable delayed hemostasis breach may manifest itself as life-threatening "invisible" retroperitoneal bleeding or a hematoma can be formed on locations other than the access site. These well-known clinical observations signify that the barrier concept has serious limitations. Today, there are no answers to these clinical observations, nor an effective way to predict, thus prevent, delayed bleeding complications.

This invention is the first to recognize that the dynamic and elastic nature of the injured vessel plays a key role in affecting and sustaining hemostasis in the vascular wound and surgical wound. This invention teaches that, while a barrier is immediately needed upon catheter removal or upon completion of a surgical intervention, to stop blood from gushing out, it is not enough to ensure hemostasis success and patient safety. This invention teaches how to use topical compressive force in an appropriate way to stop blood from gushing out upon catheter removal and, at the same time, sustain hemostasis and improve wound healing quality. This invention teaches how to timely affect and control vasculature motions to cause timely blood coagulation, how to sustain hemostasis until the fibrin clot has become stable, and how to improve wound healing quality. This invention teaches how to quench or reduce vasculature motions during the initial critical cellular phases of platelet activation, aggregation and fibrin matrix formation, as means to promote and sustain hemostasis.

This invention discloses a cooling element which provides an initial cooling profile on the injured skin surface to cause vasoconstriction and hemostasis, and a follow-on cooling profile to stabilize the injured vasculature structure to allow time for the fibrin clot to attain strength, thus reducing the potential for delayed hemostasis breach. This invention teaches a cooling profile to promote re-epithelialization, reduce scar formation and improve overall wound healing quality. This invention discloses a class of cooling materials for this application.

This invention discloses a compressive surface that is elastic to provide optimal compression, and comfort and safety to the patient. This invention discloses a compressive surface that is thermally conductive. This invention discloses a compressional force that is achieved through vertical displacement of the compression instrument, without causing lateral or transverse forces to adversely affect the wound.

This invention discloses how to use temperature to affect the injured vessel so that the vasculature structure is stabilized during the initial critical platelet aggregation and fibrin formation phase to allow a fibrin clot to attain strength to avoid unpredictable or delayed hemostasis breach. This invention discloses a therapeutic agent that affects the injured vessel so that the vasculature structure is stabilized during the initial critical platelet aggregation and fibrin formation phase to allow a fibrin clot to attain strength to avoid unpredictable or delayed hemostasis breach. This invention discloses a device and method to provide analgesic and anesthetic effect to the patient to reduce pain, reduce inflammation, reduce swelling, and reduce potential for infection. In sum, the invention device, in addition to providing an appropriate compressional force to resist blood outward flow, provides therapies to cause hemostasis, sustain hemostasis, and improve wound healing, thus achieving better clinical outcomes and reducing bleeding and reducing medical complications.

SUMMARY OF THE INVENTION

The present invention provides for a device and method that affect and control the physiological dynamic and elastic injury microenvironment to promote timely platelet aggregation, fibrin formation, blood coagulation, and to sustain hemostasis, accelerate re-epithelialization, and promote wound healing, wherein wound healing includes a hemostasis phase, an inflammation phase, a proliferation phase, a remodeling phase and a maturation phase, or any combination thereof. This invention provides an analgesic and anesthetic effect on the patient to reduce pain, reduce inflammation, reduce swelling, reduce scar formation, and reduce potential for infection.

In one aspect of the invention, the hemostasis and wound healing device is used for different types of percutaneous interventions, different types of surgical procedures and at different anatomical sites, e.g. radial access, femoral access, brachial access, hemodialysis access, various surgical incisions, and the like. In one aspect of the invention, the application of the device and a therapeutic agent on the breached injured skin surface affects and controls the vessel wound underneath the breached injured skin surface.

One aspect of the invention is a topical hemostasis and wound healing device affecting a hemostasis phase and a wound healing phase of a vascular wound or an acute surgical wound in a medical patient. Another aspect of the invention is a topical hemostasis and wound healing device where the device comprises a topical cooling compressive delivery member (hereafter "delivery member") and a therapeutic agent, where the delivery member provides cooling and a compressive force to a wound, and delivers and transports a therapeutic agent to a wound. In another aspect of the invention, the cooling compressive delivery member and the therapeutic agent affect hemostasis phase and wound healing phase.

In one aspect of the invention, the delivery member comprises a cooling compressive surface (CCS), a cooling compressive compartment (CCC), and a lateral stabilization component, or a combination thereof. In one aspect of the invention, the CCS comprises a rigid component and an elastic component. In one aspect of the invention, the CCC comprises a coolant container and a vertical displacement casing. In one aspect of the invention, the CCS is integrated into one side of the CCC during fabrication, i.e. the side facing the wound. In one aspect of the invention, the CCS is post-fabricated onto one side of the CCC, i.e. the side facing the wound. In one aspect of the invention, the coolant container in the CCC provides vertical displacement as one unit with the vertical displacement casing. In one aspect of the invention, the coolant container in the CCC performs vertical displacement independent of the vertical displacement casing, i.e. the coolant container performs vertical displacement by moving up and down relative to the vertical displacement casing, and that the casing does not move with the coolant container.

In another aspect of the invention, the CCS, or the CCC, or both, delivers and transports a therapeutic agent to the breached injured skin wound site. In another aspect of the invention, the CCS, or the CCC, or both, delivers and transports cooling to the wound site. In another aspect of the invention, the CCS is elastic and thermally conductive.

In another aspect of the invention, the delivery member delivers a compressive force to the wound site of a percutaneous wound or an acute surgical wound to resist blood from gushing out upon catheter removal or upon the completion of surgical intervention. In another aspect of the invention, the delivery member has a rigid component to resist blood outward flow. In another aspect of the invention, the delivery member has a soft and viscoelastic component providing a soft contact with the breached injured skin and the vessel wound to improve comfort and safety for the patient, thus reducing medical complications.

In another aspect of the invention, the CCS is thermally conductive. In another aspect of the invention, the CCS delivers and transports temperature from the CCC to the wound site and removes heat from the wound site. In another aspect of the invention, the CCS delivers a therapeutic agent to the wound site. In another aspect of the invention, the CCS causes hemostasis, sustain hemostasis and improve wound healing quality.

In another aspect of the invention, the CCS of the delivery member has a raised ridge substantially centered at the breached injured skin surface. In another aspect of the invention, the raised ridge of the CCS has a longitudinal length with its direction along the injured vessel under the skin. In another aspect of the invention, the CCS has a substantially conical surface with low radius of curvature, i.e. convex shape with the protruding part facing the wound. In another aspect of the invention, the CCS of the delivery member has a flat surface. In another aspect of the invention, the CCS conforms and is configured to the anatomy of the wound site.

In another aspect of the invention, the surface area of the CCS is of the same surface area as the breached skin injury. For example, if the interventional catheter is 8 F (8 French), the breached skin has an injury site of 0.27 cm in diameter and the breached skin surface area is 0.056 cm$^2$, and the CCS has a surface area of 0.056 cm$^2$. In another aspect of the invention, the CCS has a surface area between the size of the breached skin surface area and 500 times (500×) the breached skin surface area. For example, if a 8 F (8 French) catheter produces breached skin with a diameter of 0.27 cm and a surface area of 0.056 cm$^2$, the topical CCS surface area applied to the breached skin injury site can be 28 cm$^2$ (approximately 500 times of the injury surface area). In another aspect of the invention, the topical CCS surface area is 1,000 times the injured skin breached surface area.

In another aspect of the invention, the CCS surface area can be of various shapes and geometries. For example, the compressive surface area of 28 cm$^2$ can be substantially square with 5.3 cm on each side, or substantially rectangular with 4 cm on one side and 7 cm on the other side, or substantially circular with a 6 cm diameter. The large CCS surface area is to provide more even compressive pressure to the injury site so as to affect hemostasis and would healing without causing additional vessel injury or prolonged tourniquet, thus leading to medical complications. In another aspect of the invention, the large CCS surface area is to heal the vicinity of the wound affected by percutaneous access or surgery.

In another aspect of the invention, the CCS of the delivery member is configured so that the breached skin is at the center of the CCS of the delivery member. In another aspect of the invention, the CCS of the delivery member is configured so that the breached skin is off the center of the compressive delivery member.

In another aspect of the invention, the CCS in the preceding paragraphs has a flat surface. In another aspect of the invention, the CCS in the preceding paragraphs has a raised ridge where the raised ridge is centered around the breached skin. In another aspect of the invention, the CCS in the preceding paragraphs has a substantially conical surface with low radius of curvature, i.e. convex shape with the protruding part facing the wound. In another aspect of the invention, the CCS in the preceding paragraphs is configured and conforming to the anatomy of the wound site.

In another aspect of the invention, the CCS of the delivery member is a square, or substantially square, rectangular-shaped, or substantially rectangular-shaped, a square with a rounded edge, or a rectangle with a rounded edge, or a circle, or an oblong-shaped, or a substantially oblong-shaped, or an irregularly-shaped area, or the like.

In another aspect of the invention, the CCS of the delivery member is in direct contact with injured and breached skin. In another aspect of the invention, the injured and breached skin is covered with sterilized gauze or with another wound dressing, or the like, and the CCS is applied on top of the sterilized gauze or other wound dressing.

In another aspect of the invention, the CCS is soft and has a viscoelastic characteristic to provide a soft contact with the injured skin. In another aspect of the invention, the CCS is made of two layers, whereas the layer away from the breached skin is a rigid material to resist blood flow while the layer on the breached skin side, or in contact with the breached skin, is soft with a low tensile modulus and a low Young's modulus. In another aspect of the invention, the CCS is a material that has both the required rigidity to resist blood flow and the required softness to provide comfort and safety to the patient.

In another aspect of the invention, the soft component of the CCS of the delivery member is an elastomer. In another aspect of the invention, the elastomer has the tensile modulus from 50 kPa to 100 MPa. As a reference, typical human skin has the tensile strength at approximately 20 MPa and typical human vessels have the tensile strength of between 50 kPa and 3.0 MPa.

In another aspect of the invention, the CCS of the delivery member is thermally conductive. Thermal conductivity and heat exchange properties act to conduct cooling from the CCC to the wound site and to dissipate heat from the wound site. In one aspect of the invention, the thermal conductive material is a polymer. In another aspect of the invention, the thermally conductive polymer is a plastic, a natural rubber, a synthetic rubber, an elastomer, a composite, a compounded material, a blend, or a combination thereof. In another aspect of the invention, the thermal conductive polymer has a thermal conductivity between 0.15 W/(m-K) and 100 W/(m-K), where W/(m-K) is watts per meter Kelvin. In another aspect of the invention, the thermal conductive material is a metal or an alloy, known for good thermal conductivity.

In another aspect of the invention, the CCS of the delivery member incorporates a therapeutic agent, and delivers and transports a therapeutic agent to the breached injured skin to affect vessel wound and promote hemostasis, sustain hemostasis and improve wound healing quality. In another aspect of the invention, the therapeutic agent is delivered by passive means. In another aspect of the invention, the therapeutic agent is delivered by active means, for example, by applying an electrical force.

In another aspect of the invention, the therapeutic agent is selected from the group consisting of cellular proliferation inhibitor, smooth muscle inhibitor, inhibitor of vascular cell growth, anti-proliferative agent, neural blockade agent, anti-inflammatory agent, antibiotic, anesthetic agent, analgesic agent, pain killing agent, neuroprotectant, vasoconstriction agent, sclerosant agent, gene, DNA, RNA, polypeptide, protein, blood coagulation agent, platelet agent, blood-clotting agent, hemostasis agent, wound healing agent, and any combination thereof.

In another aspect of the invention, the rigid material of the CCS in the delivery member resists blood outward flow. In another aspect of the invention, the rigid material of the CCS is a metal, or an alloy. In another aspect of the invention, the rigid material is a polymer. In another aspect of the invention, the polymer is a plastic. In another aspect of the invention, the polymer is an elastomer. In another aspect of the invention, the polymer is a thermoset, a thermoplastic, a natural rubber, a synthetic rubber, a composite, a compounded material, a blend, or the combination thereof. In another aspect of the invention, the rigid polymer is thermally conductive. In another aspect of the invention, the CCS of the delivery member is a combination of the above types of materials. In another aspect of the invention, the material of the CCS is transparent or semi-transparent to enable medical personnel to conduct a visual inspection of the wound site without disturbing the wound, or without removing the device.

The rigid component of the CCS to resist blood flow can be selected from various classes of metals or metal alloys such as steel, copper, brass, titanium, titanium alloy, aluminum, iron and the like. The rigid component of the CCS to resist blood flow can also be selected from various classes of polymers such as polycarbonate, polystyrene, low-density polyethylene, high density polyethylene, polypropylene, ABS, nylon, polyethylene terephthalate, polyester and the like.

The soft and viscoelastic component of the CCS over the breached injured skin providing comfort and safety to the patient is selected from a class of natural rubber, a class of synthetic rubber, a class of silicone rubber, or other elastomers and the like. The soft and viscoelastic component of the CCS has the tensile strength between 50 kPa to 100 MPa.

In another aspect of the invention, both the rigid and the soft materials are fabricated together to attain the desired properties of resisting blood flow, providing soft contact with the injury site and providing thermal conductivity and delivering a therapeutic agent. In another aspect of the invention, the rigid and the soft materials can be two separate materials, or one single material, or one composite material that meets the application requirements. In another aspect of the invention, the rigid material is part of the coolant container.

In another aspect of the invention, a CCS is post-fabricated onto the CCC. In another aspect of the invention, the coolant dissipates cooling to the wound site in a passive conductive manner. In another aspect of the invention, the coolant dissipates cooling to the breached injury skin site by active means, for example, by electrical refrigerative force to maintain the desired cold temperature range.

In another aspect of the invention, the thermal conductive material in CCS is selected from a group of proprietary-engineered plastic or elastomers whereas the thermal conductivity is between 0.15 W/(m-K) and 100 W/(m-K).

In another aspect of the invention, the Cooling Compressive Compartment (CCC) comprises a coolant container and a vertical displacement casing. In another aspect of the invention, the coolant container contains a coolant at the temperature lower than the body temperature. In another aspect of the invention, the vertical displacement casing engages the coolant container and provides vertical displacement mechanism to the coolant container. In one aspect of the invention, the coolant container and the vertical displacement casing perform vertical displacement as one unit. In one aspect of the invention, the coolant container performs vertical displacement independent of the vertical displacement casing. In other words, the coolant container performs vertical displacement by moving up and down relative to the vertical displacement casing and the vertical movement causes the coolant container to move towards or away from the wound site. In one aspect of the invention, the coolant container containing coolant is situated above the wound site and provides unhindered cooling to the wound.

In another aspect of the invention, the CCC material is a metal, or a metal alloy. In another aspect of the invention, the CCC material is a polymer. In another aspect of the invention, the CCC material is a plastic. In another aspect of the invention, the CCC material is an elastomer, for example without limitation, a natural rubber, or a synthetic rubber, or the like. In another aspect of the invention, the CCC material is a woven fabric, or a non-woven. In another aspect of the invention, the CCC material comprises one or more of the following materials: a metal, a plastic, an elastomer, a fabric, a non-woven, or a combination thereof.

In another aspect of the invention, the CCC material is selected to provide thermal conductivity on the side of the CCS over the breached injury skin side, and to provide thermal insulation on all other sides outside of the CCS side to avoid heat loss, where "heat loss" means the loss of coolant capacity to the ambience. In another aspect of the invention, the material of CCC is transparent or semi-transparent to enable medical personnel to conduct visual inspection of the wound site without disturbing the wound, or without removing the device.

In another aspect of the invention, the material for CCC components provides thermal insulation to prevent the coolant from losing heat (i.e. losing cooling in this instance) to the ambience. In another aspect of the invention, all components in the CCC, except the surface facing the wound, are to provide thermal insulation to the coolant to maintain coolant capacity and to prevent coolant losing cooling to the ambience.

In another aspect of the invention, the coolant is contained inside the coolant container and in direct contract with the container. In another aspect of the invention, the coolant is contained inside a thin film and the thin film containing the coolant is then placed inside the coolant container.

In another aspect of the invention, the coolant container is substantially spherical, or substantially cylindrical, or substantially square, or substantially rectangular, or substantially cubical, or irregularly shaped container, or the like. In another aspect of the invention, the coolant container is a closed structure and the liquid coolant is injected into the container with a syringe type of instrument. In another aspect of the invention, the coolant container is with one side open and the coolant, either in a liquid or in a solid form, either directly or already-contained in a thin-film pouch, is placed onto the container before the top cap is placed on top of the container and the container is sealed afterwards.

In another aspect of the invention, the thin film is a plastic material. In another aspect of the invention, the thin film is a rubbery material. In another aspect of the invention, the thin film is flexible. In another aspect of the invention, the thin film is chemical and corrosion resistant. In another aspect of the invention, the thin film is polyethylene, polypropylene, polyurethane, or silicone or the like.

In another aspect of the invention, the coolant container has a flat surface on the wound site. In another aspect of the invention, the coolant container has a soft conforming surface on the wound site. In another aspect of the invention, the soft conforming surface has a raised ridge approximately centering at the injury site. In another aspect of the invention, the soft conforming surface is conically shaped with a low radius of curvature. In another aspect of the invention, the soft conforming surface is anatomically conforming. In another aspect of the invention, the soft conforming surface is thermally conductive.

In another aspect of the invention, the coolant container is engaged to a vertical displacement casing so that the coolant container is raised from (releasing compressive pressure), or lowered to (increasing compressive pressure) the breached injured skin, and the vertical displacement of the coolant container is controlled by the casing and yet the movement of the coolant container is independent of the casing. In other words, the casing stays stationary and does not encounter vertical displacement during the application of the compressive pressure and the coolant container is moving up and down relative to the casing. In another aspect of the invention, the independent vertical displacement mechanism of the coolant container provides a substantially vertical-direction-only compression through vertical-movement-only of the coolant container.

In another aspect of the invention, the vertical-movement-only design produces no outward lateral, transverse or twisting compressive actions on the breached injury skin, thus avoiding additional injury to the wound. In another aspect of the invention, the vertical displacement of the coolant container is precisely controlled to allow precise control of the amount of compressive force applied to the breached injured skin and the vessel wound. In another aspect of the invention, the vertical displacement of the coolant container is reversible in a precise incremental manner to reduce compressive pressure at the wound site as the wound heals. The controlled partial release of compressive pressure at the wound site upon wound healing facilitates hemostasis, wound healing and reduces pain.

In another aspect of the invention, the extent of vertical displacement of the coolant container depends on the type of injury. In another aspect of the invention, the vertical displacement of the coolant container is between 0.2 mm to 3.0 cm. In another aspect of the invention, the vertical displacement of the coolant container produces a compressive pressure between 0.2 psi (pounds per square inch) to 20 psi. As a reference, a typical human arterial blood pressure of 180 mmHg is 3.5 psi.

In another aspect of the invention, the applied compressive pressure is initially greater (the depressed lower position of the coolant container) to resist blood flow upon catheter removal. In another aspect of the invention, the applied compression pressure is reduced over time upon blood coagulation and wound healing. In another aspect of the invention, the applied compression pressure is less (the raised higher position of the coolant container) as the coagulation process is progressed to completion and a stable fibrin clot is formed.

In another aspect of the invention, the device is applied between 5 minutes to 8 hours depending on the type of the injury. In another aspect of the invention, the device is left on the patient overnight per hospital protocol. In another aspect of the invention, the device comprises a CCC where the CCC is changed every hour, or every three hours, or to the extent necessary to maintain passive cooling. In another aspect of the invention, the device is left on the patient after the coolant has reached ambient temperature. In another aspect of the invention, the device is left on the patient after the coolant has reached the body temperature.

In another aspect of the invention, the coolant comprises a temperature profile on the breached injured skin. In another aspect of the invention, the coolant temperature profile comprises an initial temperature profile and a follow-on temperature profile on the injured skin surface. In another aspect of the invention, the initial temperature profile at the breached injured skin is between +5° C. to +20° C. for a duration of up to 10 minutes. As a reference, a typical unbroken skin surface temperature in a temperature-controlled room is between 30° C.-33° C.

In another aspect of the invention, the follow-on temperature profile is between +10° C. to +25° C. for a duration of between 5 minutes and 20 hours. In another aspect of the invention, the follow-on temperature profile is maintained within the range of ±10° C. before warming to ambient temperature. In another aspect of the invention, the coolant container, or the CCC, or both, are changed before, or shortly after, the follow-on temperature reaches ambient temperature. In another aspect of the invention, the cooling temperature profile does not cause skin irritation or cold blisters.

In another aspect of the invention, the temperature has more than 2 different temperature zones to promote cellular activity and migration at the wound site, thus promoting coagulation processes and wound healing. In another aspect of the invention, the temperature in each zone is altered by an active means, for example without limitation, an electronically-controlled temperature device. In another aspect of the invention, the temperature in each zone is altered by using a different type of coolant. In another aspect of the invention, the temperature of one zone is altered depending on the temperature of other zones. In another aspect of the invention, the temperature of one zone is altered independent of the temperature of other zones, for example, without limitation, the temperature of a center zone is different from the temperature of the surrounding zones. In another aspect of the invention, the plurality of zones is selected according to the size or the nature of the wound.

In another aspect of the invention, cooling suppresses vasculature motions to provide a more stabilized microenvironment of the vascular injury site (below the skin) to allow platelet aggregation and fibrin formation to take place and to allow a fibrin clot to become stable, without agitation or disruption, and sustain hemostasis.

In another aspect of the invention, the coolant is a liquid. In another aspect of the invention, the coolant is a solid. In another aspect of the invention, the coolant is a sludge. In another aspect of the invention, the coolant is a gel. In another aspect of the invention, the coolant changes phases, for example melting from solid to liquid, during application.

In another aspect of the invention, the coolant is water. In another aspect of the invention, the coolant is water containing at least one electrolyte, for example, calcium chloride, or ammonium nitrate. In another aspect of the invention, the coolant is water containing a water-soluble or a water-dispersible polymer, for example, sodium carboxymethyl cellulose, cellulose ether, guar gum, sodium polyacrylate, polysaccharide, and the like. In another aspect of the invention, the initial coolant can be refrigerated or frozen prior to use. In another aspect of the invention, the coolant is activated by an electrical force.

In another aspect of the invention, the coolant is selected from a class of Phase Change Material (PCM) capable of maintaining a narrow melting temperature range at the selected temperature range. The PCM is capable of absorbing or releasing relatively large amounts of latent heat at a relatively constant temperature, typically referring to melting from solid to liquid or solidifying from liquid to solid. In another aspect of the invention, the PCM is a salt hydrates. In another aspect of the invention, the coolant is a bio-based fat, fatty acid, ester, or oil and the like. In another aspect of the invention, the coolant is a petroleum-based synthetic alkane, ester, mineral oil, paraffin, other organic derivative, and the like. In another aspect of the invention, the melting temperature of the PCM is selected between −15° C. and +25° C. In another aspect of the invention, a PCM material can be used singularly or in combination with another PCM material.

In another aspect of the invention, the volume of the coolant is dependent on the nature of the injury, the therapy surface area and the duration of the therapy. In another aspect of the invention, the volume of the coolant to the affected breached skin site is between 3 $cm^3$ to 500 $cm^3$. In another aspect of the invention, the coolant can transfer cooling to the wound site in a passive manner. In another aspect of the invention, the coolant can be controlled by electrical means to produce a desired temperature on the breached injured skin for a desired duration. In another aspect of the invention, the electronic control electronically controls and administers the cooling temperature to the wound site for a certain duration according to a wound healing phases.

In another aspect of the invention, the initial temperature of the coolant upon application to a medical patient is provided by the electrical refrigerative force. In another aspect of the invention, the initial temperature of the coolant upon application to a medical patient is provided by refrigerating the device or the CCC in a refrigerator or a freezer.

In another aspect of the invention, the delivery member comprises a lateral stabilization component. In another aspect of the invention, the lateral stabilization component comprises a mechanism to apply even and appropriate compression forces in the opposite lateral direction to return the injury flap to its anatomical position to promote wound healing. The application of the lateral direction stabilization is in the direction of pulling the injury flap together, but not to pull it apart. In another aspect of the invention, both ends of the lateral stabilization component are fastened together, for example, without limitation, by a support connector such as Velcro®, adhesive tape, D-ring, or the like.

In another aspect of the invention, the lateral stabilization component is made of a stretchable fabric. In another aspect of the invention, the lateral stabilization component is made of a non-stretchable fabric. In another aspect of the invention, the lateral stabilization component is made of a stretchable non-woven, or a non-stretchable non-woven. In another aspect of the invention, the lateral stabilization component is made of a synthetic material. In another aspect of the invention, the lateral stabilization component is made of a natural material. In another aspect of the invention, the lateral stabilization is conforming to the anatomy of the injury site and the anatomy of the injury vicinity.

In another aspect of the invention, the lateral stabilization component is structurally engaged to the CCC and the CCS. In another aspect of the invention, the lateral stabilization component is structurally independent of the CCC and independent of the CCS. In another aspect of the invention, the lateral stabilization component provides mechanism to avoid compression on the backside of the wound, thus avoiding tourniquet and reducing discomfort to the medical patient.

With those and other objects, advantages and features on the invention that may become hereinafter apparent, the nature of the invention may be more clearly understood by reference to the following detailed description of the invention, the appended claims, and the drawings attached hereto.

BRIEF DESCRIPTION OF THE DRAWINGS

The accompanying drawings, which are incorporated herein and form part of the specification, illustrate various embodiments of the present invention and together with the description, further serve to explain the principles of the invention and to enable a person skilled in the pertinent art to make and use the invention. In the drawings, like reference numbers indicate identical or functionally similar elements. A more complete appreciation of the invention and many of the attendant advantages thereof will be readily obtained as the same becomes better understood by reference to the following detailed description when considered in connection with the accompanying drawings, wherein:

FIG. 7 is another exemplary embodiment of the lateral stabilization component where FIG. 7A a lateral stabilization component prior to application and FIG. 7B a lateral stabilization component in use.

FIG. 8 is an exemplary embodiment of a hemostasis and wound healing device as applied to the percutaneous radial access site, where FIG. 8A an exemplary embodiment of the device prior to application to the wound site and FIG. 8B an exemplary embodiment of the device in use. The coolant container in FIG. 8B is vertically depressed from the original configuration relative to the casing in FIG. 8A. FIG. 8C is a computer-rendered device as applied to heal a percutaneous radial access site wound.

DETAILED DESCRIPTION OF THE INVENTION

Figure 1:
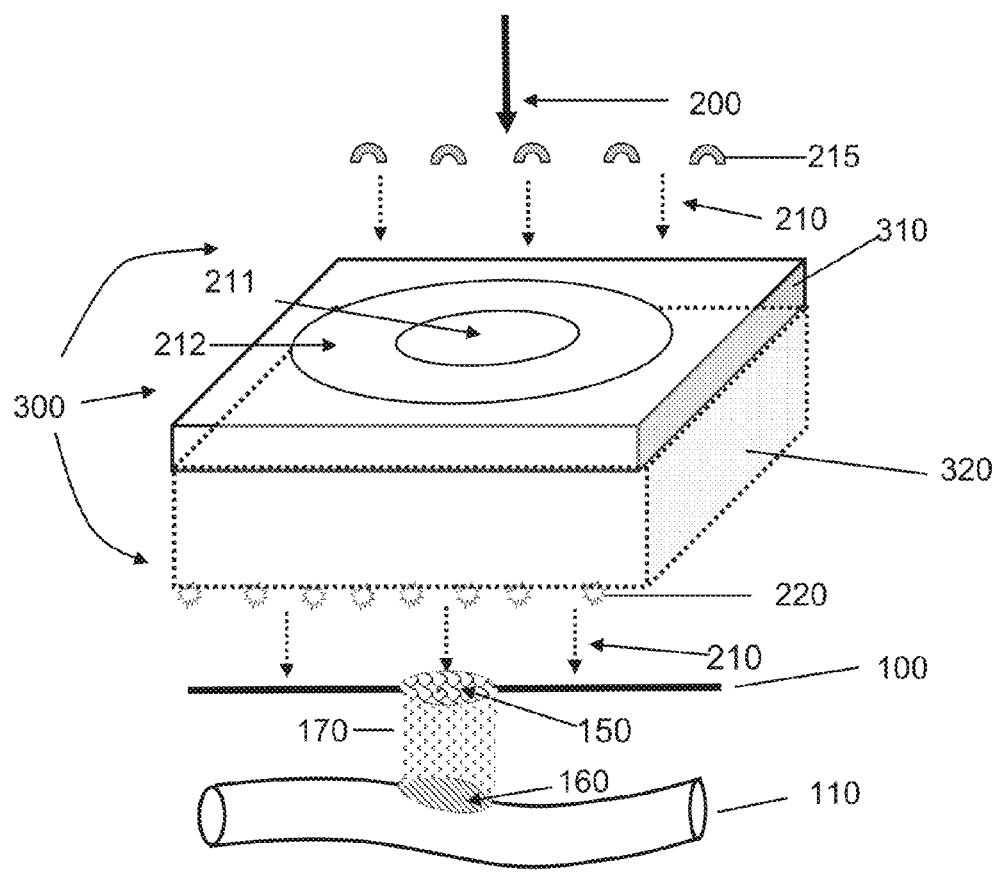
FIG. 1 is a graphical representation of an exemplary embodiment of a cooling compressive surface (CCS) of the delivery member and its functions and components.

In the following detailed description, reference is made to the accompanying drawings which form a part hereof and in which is shown by way of illustration specific embodiments in which the invention may be practiced. These embodiments are described in sufficient detail to enable those skilled in the art to practice the invention, and it is to be understood that other embodiments may be utilized and that structural or logical changes may be made without departing from the scope of the present invention. The following detailed description is, therefore, not to be taken in a limiting sense, and the scope of the present invention is defined by the appended claims.

In the past, interventions of a cardiovascular disease or the design of a vascular device has treated the diseased vascular segment as a rigid and stationary structure with constant dimensions. As such, precision deployment and precision fitting to the diseased vascular segment become the paramount, and sometimes the only, concern. However, ample clinical experiences and a large amount of population-based statistics have shown that these interventional devices often fail for unknown reasons and in many cases, medical complications remain unabated for decades. These clinical observations are particularly true for the bleeding and vascular complications in percutaneous femoral access interventions.

Because the injured vessel is dynamic and elastic, as a result, no amount of precision deployment and precision fitting, as currently practiced, to "anchor, plug or seal" a vascular wound is sufficient to ensure patient safety and procedural success. The lack of real progress in percutaneous hemostasis is supported by many well-known and troublesome clinical observations including the unpredictable, delayed breach of hemostasis. Bleeding and vascular complications in these situations are often medical emergencies, not only undermining the patient's safety, but also becoming a significant societal economic burden.

This invention is the first to recognize that these seemingly subtle vasculature motions and the elastic nature of the injured vessel have a particular effect on the clinical outcomes of hemostasis in a percutaneous intervention or in a surgical wound, and suggests particular means to solve the identified problems. Even though this invention focuses on the design and methods of use of a topical device applied outside-of-the-body over the breached skin surface, this invention recognizes that the wound is on the vasculature (often a major artery or a major vein) under the skin, and the topical device of the invention is designed to affect and heal the injured vessel under the skin.

This invention teaches how to affect and control vasculature motions and other motions in the muscular/skeletal structures surrounding the injury site, particularly during the critical initial phase of platelet aggregation and fibrin clot formation. Without successful completion of these initial cellular steps, follow-on wound healing phases will be compromised, or not taking place properly. But once these initial cellular steps are completed without disruption and without agitation, the follow-on wound healing phases become a manageable process and a natural progression of the initial successful hemostasis.

By "hemostasis phase" is meant a visual determination that no blood is flowing or oozing out on the skin surface and that sufficient time has elapsed to allow a fibrin clot to become stable to minimize rebleeding.

By "wound healing phase" is meant any phase or related phases in the wound healing process including vasculature motions, hemostasis, blood coagulation, platelet aggregation, fibrin formation, re-epithelialization, inflammation, scar formation, proliferation, remodeling and maturation, or the like.

By "vasculature motions" or "vascular motions" is meant any motions associated with the vascular system and with the local vascular segment including vasomotions, vasoconstriction, vasodilation, vasospasm and the like.

By "wound site" or "injury site" is meant the vascular wound and the skin wound together. Even though the device is applied topically on the skin and outside of the body, the device is meant to affect the vessel wound under the skin.

By "coolant" is meant a material that is kept at a low temperature, as specified in this invention and typically lower than the body temperature, prior to the application to a wound site to affect hemostasis and wound healing. The coolant's low temperature may be maintained by an active means, such as an electrical force. Or the coolant, during application, gradually attains temperature equilibrium by heating up to the ambient temperature or to the body temperature of a medical patient. The coolant functions to keep the affected body area at a lower temperature by absorbing, thus removing, heat from the injury site.

By "Phase Changing Material, PCM" is meant a material that melts or solidifies at a narrow temperature range and is capable of storing and releasing large amounts of energy upon phase change.

The present invention provides means to affect and control vasculature motions during the initial critical phase of platelet aggregation and fibrin formation upon catheter removal or upon surgery completion, to cause hemostasis, blood coagulation, platelet aggregation and fibrin formation, to maintain and sustain hemostasis, to promote re-epithelialization and wound healing, to reduce pain, swelling, inflammation and scar formation, and to improve overall wound healing quality, or any combination thereof.

With reference to one embodiment, FIG. 1 is a graphical representation of the cooling compressive surface (CCS) 300 of the delivery member. An unbroken skin 100 can have a breached injured skin wound 150. Underneath the skin, blood vessel 110 can have a vascular wound 160. Connecting the skin wound 150 and the vessel wound 160, the tissue track wound is 170. The wound can be a puncture, a surgical incision, vessel rupture, laceration, or the like.

The cooling compressive surface CCS 300 delivers and transports a compressive pressure 200 to the wounds 150, 160, and 170. The CCS further delivers and transports cooling from coolant 215 to the wounds 150, 160, and 170 in the direction of 210. The CCS incorporates a pharmaceutical agent 220 which is delivered and transported to the wounds 150, 160, and 170. The cooling direction 210, as delivered and transported by coolant 215 in CCS 300, can be further divided into zones with different temperatures in different zones. For example, without limitation, the first zone 211 is at the central portion of the CCS 300 and the second zone 212 outside of zone 211 covering the outside portion of the CCS 300. The temperature zones can take a variety of shapes and sizes corresponding to the use, for example, without limitation, substantially circular, substantially square, substantially rectangular, polygon, or the like. The temperature of each zone can be altered according to the temperature of other zones. The temperature of each zone can also be altered independent of the other sections depending on use requirements. Alternatively, the plurality of zones is selected according to the nature of the wound and the anatomical location of the wound.

The delivery and transport of compressive pressure 200, coolant 215 in the cooling direction 210, and a pharmaceutical agent 220, from the skin wound 150 to the vascular wound 160 through the tissue track wound 170 can be by a passive diffusive means, or by an active means such as by applying an electrical source. The compressive pressure 200, coolant 215 and pharmaceutical agent 220 can individually, or together, affect the wound and promote hemostasis and wound healing.

In one embodiment, the CCS 300 can comprise two layers. In one embodiment, the first layer 310 is rigid with certain rigidity and flexural strength to affect a compressive pressure between 0.2 psi and to 20 psi. As a reference, a typical human arterial blood pressure of 180 mmHg is 3.5 psi. In one embodiment, the second layer 320 is soft, flexible and elastic with a tensile modulus from 50 kPa to 100 MPa. As a reference, typical human skin has a tensile strength of approximately 20 MPa and typical human vessels have the tensile strength of between 50 kPa and 3.0 MPa. In one embodiment, the first layer 310 is thermally conductive, or the second layer 320 is thermally conductive, or both layers are thermally conductive. At least one of the layers 310 and 320 in CCS 300 has a thermal conductivity of between 0.15 W/(m-K) and 100 W/(m-K).

The rigid first layer 310 in the CCS 300 serves to resist blood outward flow upon catheter removal or upon surgery completion, and the soft, elastic and thermally-conductive second layer 320 in CCS 300 conforms to the injury site and serves to provide comfort, cooling and therapy to the patient, thus improving the patient's clinical outcome. The rigid first layer 310 can be part of the structure in the coolant container 410 in FIG. 2.

The surface area of the CCS 300 can be identical to the surface area of the skin wound 150, or up to 1,000 times larger than the surface area of the skin wound 150. The large surface area of CCS 300 is to provide therapy to heal the vasculature and tissue structures surrounding the wound. The wound 150 can be at the center of the CCS 300, or off the center of the CCS 300, depending on the goal of the therapy.

The CCS 300 in FIG. 1 can take any shape that allows for achieving the therapeutic goal depending on the nature of the injury and the anatomical location of the injury; for example, without limitation, substantially rectangular, substantially square, substantially cylindrical, substantially round, or the like. The CCS 300 can be shaped to accommodate the injury anatomy, or shaped to accommodate a specific type of injury. The CCS 300 can also have a longer dimension along the injured vessel direction.

The first layer 310 and second layer 320 of the CCS 300 can be made of the same material, or of different materials. The first layer 310 can be a metallic material. The metal can be an elemental metal or an alloy. The elemental metal and metal alloy can be selected from a variety of classes such as steel, copper, brass, titanium, titanium alloy, aluminum, iron and the like. The first layer 310 can be a polymer and the polymer can be a plastic, a composite, a compounded material, a blend, a high-durometer elastomer, or the combination thereof. The polymer can be selected from a variety of classes including, without limitation, polycarbonate, polystyrene, low-density polyethylene, high density polyethylene, polypropylene, polyurethane, polyvinylchloride, polyvinyl alcohol, ABS, neoprene, nylon, polyethylene terephthalate, polyethylene glycol, poly-vinyl-pyrrolidone and methacrylates, ethylene vinyl acetate, polytetrafluoroethylene, expanded polytetrafluoroethylene, fluorinated polymer, fluorinated elastomer, polyolefin, silicon-containing polymer, polyacrylamide, polycrylonitrile-polyacrylamide, polyester, polysilicone, a mixture of the aforementioned biocompatible materials, or the like.

The first layer 310 can be an elastomer, for example without limitation, a natural rubber, a synthetic rubber, or a combination thereof. The elastomer can be selected from a variety of classes such as polyurethane, silicone, neoprene, or other specialty or proprietary materials such as thermal-conductive silicone or thermal conductive polymer, for example without limitation, CoolPoly®.

The second layer 320 can be a metallic material. The metal can be an elemental metal or an alloy. The elemental metal and metal alloy can be selected from a variety of classes such as steel, copper, brass, titanium, titanium alloy, aluminum, iron and the like. The second layer 320 can be a polymer and the polymer can be a plastic, a composite, a compounded material, a blend, an elastomer or the combination thereof. The polymer can be selected from a variety of classes including, without limitation, polycarbonate, polystyrene, low-density polyethylene, high density polyethylene, polypropylene, polyurethane, polyvinylchloride, polyvinyl alcohol, ABS, nylon, polyethylene terephthalate, polyethylene glycol, poly-vinyl-pyrrolidone and methacrylates, ethylene vinyl acetate, polytetrafluoroethylene, expanded polytetrafluoroethylene, fluorinated polymer, fluorinated elastomer, polyolefin, silicon-containing polymer, polyacrylamide, polycrylonitrile-polyacrylamide, polyester, polysilicone, a mixture of the aforementioned biocompatible materials, or the like.

The material of the second layer 320 can be an elastomer, for example without limitation, a natural rubber, a synthetic rubber, or the combination thereof. The elastomer can be selected from a variety of classes such as polyurethane, silicone, neoprene, or other specialty or proprietary materials such as thermal-conductive polymer, for example without limitation, CoolPoly®. Alternatively, the material of cooling compressive surface CCS 300 and its components 310 and 320 is transparent or semi-transparent to enable medical personnel to conduct visual inspection of the wound site without disturbing the wound, or without removing the device. Alternatively, the material of the second layer can be a fabric or a non-woven.

The therapeutic agent 200 can be any agent that affects and controls vasculature motions in the hemostasis phase and the wound healing phases, and promote all wound healing phases and related phases. The therapeutic agent is selected from the group consisting of cellular proliferation inhibitor, smooth muscle inhibitor, inhibitor of vascular cell growth, anti-proliferative agent, neural blockade agent, anti-inflammatory agent, antibiotic, anesthetic agent, analgesic agent, pain killing agent, neuroprotectant, vasoconstriction agent, sclerosant agent, gene, DNA, RNA, polypeptide, protein, blood coagulation agent, platelet agent, blood-clotting agent, hemostasis agent, wound healing agent, and any combination thereof.

Alternatively, the therapeutic agent 220 can be a compound that inhibits cellular proliferation, for example, without limitation, paclitaxel, rapamycin, actinomycin D, methotrexate, doxorubicin, sirolimus, cyclophosphamide, and 5-fluorouracil, 6-mercapatopurine, 6-thioguanine, a mitotic inhibitor, cytoxan, cytarabinoside, cis-platin, alcohol, arsenic trioxide, bleomycin, captothecin, capecitabine, carmustine, celecoxib, daunorubucin, docetaxel, etoposide, exemestane, fludarabine, gemcitabine, hydroxyurea, idarubicin, irinotecan, ifosfamide, letrozole, leucovorin, mitoxantrone, pamidronate, pentostatin, porfirmer sodium, streptozotocin, tamoxifen, temozolamide, tenopside, topotecantoremifene, tretinoin, valrubicin, vinorelbine, zoledronate, altretamine, anastrozole, bexarotene, carboplatin, everolimus, chlorambucil, busulfan, or the like.

Alternatively, the therapeutic agent 220 can be a smooth muscle inhibitor, for example, without limitation, an agent that modulates intracellular calcium binding proteins, a receptor blocker for contractile agonists, an inhibitor of the sodium/hydrogen antiporter, a protease inhibitor, a nitrovasodilator, a phosphodiesterase inhibitor, a phenothiazine, a growth factor receptor agonist, an anti-mitotic agent, a growth factor receptor antagonist, an immunosuppressive agent, a steroid such as estrogen, hydrocortisone or dexamethasone, a protein kinase inhibitor, or the like.

Alternatively, the therapeutic agent 220 can be an inhibitor of vascular cell growth, for example, without limitation, a growth factor inhibitor, a growth factor receptor antagonist, a transcriptional repressor, a translational repressor, an antisense DNA, an antisense RNA, synthetic DNA compounds, especially those with backbones that have been modified to inhibit enzymatic degradation (e.g. phosphorothioate compounds and morpholino diamidate compounds), a replication inhibitor, an inhibitory antibody, an antibody directed against growth factors, a bifunctional molecule consisting of a growth factor and a cytotoxin, and a bifunctional molecule consisting of an antibody and a cytotoxin, double stranded DNA, single stranded DNA, single stranded RNA and a double stranded RNA, a single-stranded DNA molecule, a double-stranded DNA molecule, a single-stranded RNA molecule, a double-stranded RNA molecule, or the like.

Other non-limiting examples of other therapeutic agents 220 that can be delivered or transported using the present invention include the classes of anesthetic, neural blockade agent, analgesic and pain killing agent such as lidocaine, prilocaine, epinephrine, ropivacaine bupivacaine, propofol, mepivacaine, midazolam, fentanyl, morphine, oxycodone, methadone and related compounds, anti-fungal agents such as fluconazole and related compounds; anti-viral agents such as trisodium phosphomonoformate, trifluorothymidine, acyclovir, ganciclovir, DDI and AZT; cell transport/mobility impending agents such as colchicine, vincristine, cytochalasin B and related compounds; antihypertensives; decongestants such as phenylephrine, naphazoline, and tetrahydrazoline; immunological response modifiers such as cyclosporin, muramyl dipeptide and related compounds; peptides and proteins such as insulin, growth hormones, insulin related growth factor, heat shock proteins and related compounds; steroidal compounds such as dexamethasone, prednisolone and related compounds; low solubility steroids such as fluocinolone acetonide and related compounds; carbonic anhydrase inhibitors; diagnostic agents; antiapoptosis agents; gene therapy agents; sequestering agents; reductants such as glutathione; antipermeability agents; antisense compounds; antiproliferative agents; antibody conjugates; bloodflow enhancers; antiparasiticagents; non-steroidal anti inflammatory agents such as ibuprofen, indomethacin; nutrients and vitamins: enzyme inhibitors: antioxidants; anticataract drugs; aldose reductase inhibitors; cytoprotectants; cytokines, cytokine inhibitors, and cytokin protectants; mast cell stabilizers; and anti neovascular agents such as pigment epithelium derived growth factor (PEDF), PEDF-expressing gene vectors such as adenovirus-PEDF, inhibitors of vascular endothelial growth factor and fibroblast growth factor, matrix metalloproteinase inhibitors, or the like.

Alternatively, the therapeutic agent 220 can be a neuroprotectant, for example, without limitation, nimodipine and related compounds; an antibiotic such as tetracycline, chlortetracycline, bacitracin, neomycin, polymyxin, gramicidin, oxytetracycline, chloramphenicol, gentamycin, and erythromycin; sulfonamides, sulfacetamide, sulfamethizole, sulfisoxazole; nitrofurazone, and sodium propionate; an anti-allergenic such as a histamine receptor blocker; an anti-inflammatory such as hydrocortisone, hydrocortisone acetate, dexamethasone 21-phosphate, fluocinolone, medrysone, methyiprednisolone, prednisolone 21-phosphate, prednisolone acetate, fluoromethalone, betamethasone and triminolone; a miotic and anticholinesterase such as pilocarpine, eserine salicylate, carbachol, di-isopropyl fluorophosphate, phospholine iodine, and demecarium bromide; mydriatics such as atropine sulfate, cyclopentolate, homatropine, scopolamine, tropicamide, eucatropine, and hydroxyamphetamine; svmpathomimetics such as epinephrine, or the like.

Alternatively, the therapeutic agent 220 can be a vasoconstriction agent, for example, without limitation, an adrenergic agonist, adrenaline, epinephrine, norepinephrine, dopamine, thromboxane, endothelin, angiotensin, asymmetric dimethylarginine, arginine, vasopressin, argipressin, antidiuretic hormone, thrombin, methylphenidate, amphetamines, methylphenidate, mephedrone, oxymetazoline, phenylephrine, propylhexedrine, pseudoephedrine; or the like.

Alternatively, the therapeutic agent 220 can be a sclerosant agent, for example, without limitation, ethanolamine, sodium tetradecyl sulfate, ethanolamine oleate, ethanol, absolute alcohol, polidocanol, thrombin, fibrin glue, saline, adrenaline, sodium carbonate, sodium salicylate, quinine, or any combination such as 1:100,000 adrenaline and 5% ethanolamine, and the like.

Other agents may be employed for a variety of purposes. For example, without limitation, buffering agents, electrolytes and preservatives may be employed. Buffering agents may be, for example, without limitation, sodium carbonate, sodium borate, sodium phosphate, sodium acetate, sodium bicarbonate, tris-borate, or the like. Electrolytes such as sodium chloride and potassium chloride and the like may also be included in the formulation. Preservatives may be, for example, without limitation, sodium bisulfite, sodium bisulfate, sodium thiosulfate, benzalkonium chloride, chlorobutanol, thimerosal, phenylmercuric acetate, phenylmercuric nitrate, methylparaben, polyvinyl alcohol and phenylethyl alcohol.

Alternatively, temperature cooling direction 210 can be generated by various coolants 215 and delivered and transported to the wound site in a passive diffusive manner. Temperature can also be generated by an active refrigerative instrument such as a battery or AC-powered cooling instrument and delivered and transported to the wound site.

Temperature generated by the coolant 215 is to lower temperature at the breached skin surface of the injury site. In one embodiment, the temperature profile reflects a temperature that alters as a function of time corresponding to the wound healing phases. In one embodiment, the temperature profile corresponds to the temperature requirement of each hemostasis phase and wound healing phase in the wound healing process, and corresponds to the time requirement of each hemostasis phase and wound healing phase. Alternatively, the temperature profile corresponds to the temperature requirement of a single wound healing phase of the wound healing process.

Figure 2:
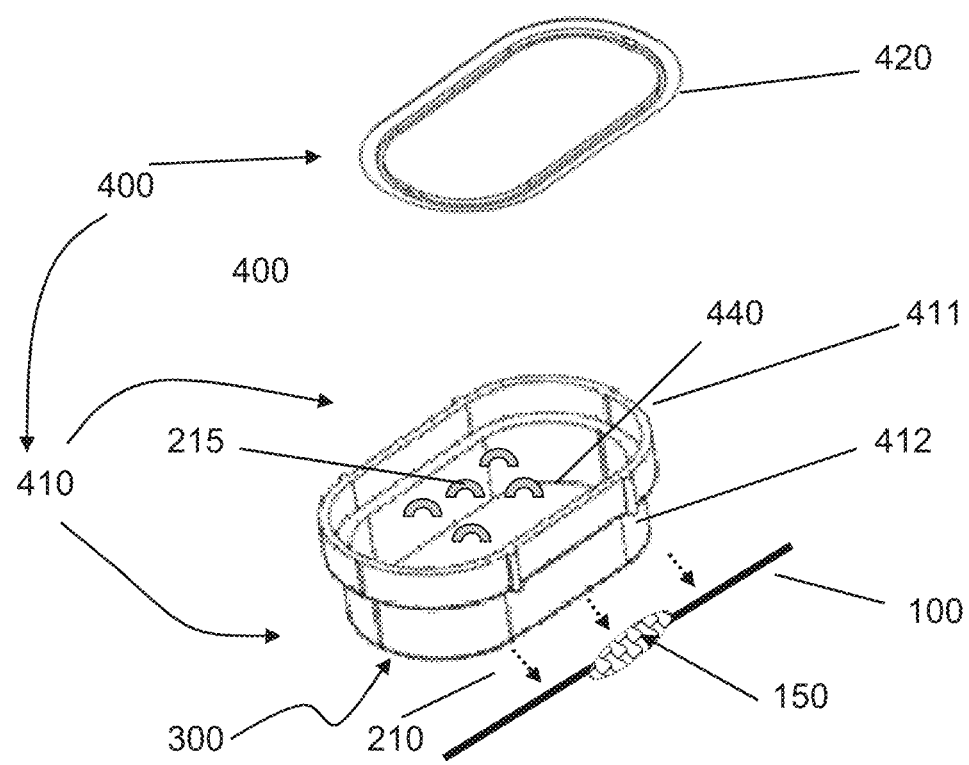
FIG. 2 is an exemplary embodiment of an exploded view of the components of the coolant container and its cover of the cooling compressive compartment (CCC).

In one embodiment, the coolant 215 can be contained in the coolant container 400 depicted in FIG. 2. In one embodiment, the coolant container 400 can be a sealed container. In one embodiment, the coolant container 400 can have two components, a reservoir 410 and a cap 420. The reservoir 410 can have two different circumferences, i.e. the top portion 411 with a bigger circumference and the bottom portion 412 with a smaller circumference. The total height of 412 is the total vertical displacement, and the vertical displacement is the mechanism by which compressive pressure is applied to the wound site and modulated at the wound site. The reservoir 410 can contain coolant 215 for the volume of 440. The bottom surface of coolant container 400 facing the wound 150 is the cooling compressive surface CCS 300. CCS 300 can either be pre-fabricated as part of the coolant container 400, or post-fabricated onto the coolant container 400. CCS 300 and coolant container 400 together deliver and transport temperature and a therapeutic agent to the wound site 150.

The coolant 215 can be a liquid or a solid. The coolant 215 can be placed onto the reservoir 410 directly or placed inside of a thin film membrane, similar to a water balloon, before placing the coolant-in-thin-film into the reservoir 410. The coolant 215 can be prepared, such as by refrigeration or by freezing, prior to application. The coolant 215 can provide cooling to the wound site through passive means, such as passive diffusion or radiation. The coolant temperature can also be actively maintained and controlled by an AC or a DC-powered refrigerating instrument. The electrically controlled coolant can control, monitor and administer the delivery of temperature as a function of time, and the delivered temperature can be according to a wound healing profile.

The bottom side CCS 300 facing the wound of the coolant container 400 is thermally conductive, while all other sides of CCS 300 and coolant container 400 are thermally insulated to prevent "heat loss" to the ambience where "heat loss" means coolant 215 loses its cooling capacity by warming up to the ambient temperature.

The coolant 215 can be pure water or water containing at least one electrolyte, for example without limitation, calcium chloride, or ammonium nitrate and the like. The coolant 215 can also be water containing a water-soluble or a water-dispersible polymer or a mixture of such polymers, for example without limitation, sodium carboxymethyl cellulose, cellulose ether, guar gum, sodium polyacrylate, polysaccharide, and the like.

The coolant 215 can also be selected from a class of Phase Change Material (PCM) capable of maintaining a narrow melting temperature range at a selected temperature range. The cooling material can be a bio-based fat, fatty acid, ester, or oil, and the like. The cooling material can also be a petroleum-based synthetic alkane, ester, paraffin, mineral oil, or other organic derivative, and the like. The cooling materials can be used singularly or in combination, depending on application needs. When using PCM as a coolant 215 for this application, the melting temperature selected is between −15° C. to +25° C. Prior to application, the temperature of coolant 215 can be maintained in a cooler, such as a refrigerator or a freezer.

The temperature at the breached skin surface and the coolant temperature are related to each other by a variety of factors such as the amount (volume) and the nature (specific heat, or latent heat) of the coolant 215, the design parameters and the material selection of the cooling compressive surface CCS 300, and the design parameters and the material selection of the coolant compartment 400, and the like. The design parameters and the material selections are such that the temperature on the skin surface does not cause redness or cold blisters after device application. One embodiment of the temperature profile at the breached injured skin surface 150 as a function of time is shown in FIG. 3.

Figure 3:
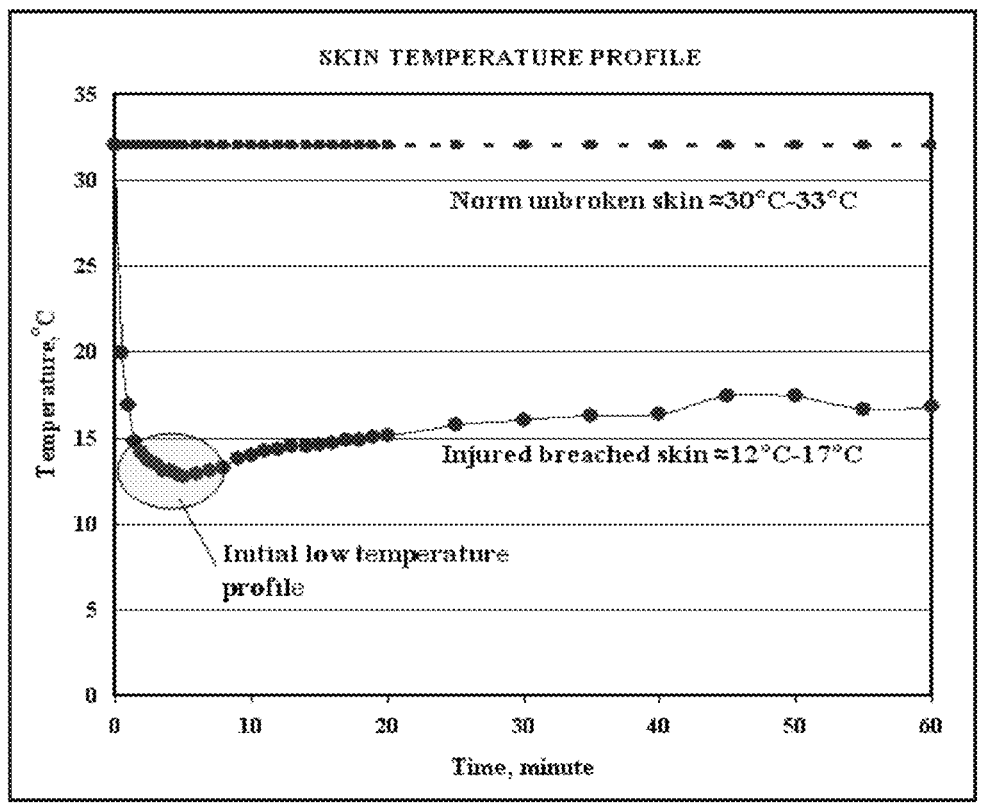
FIG. 3 is an exemplary embodiment of the skin temperature profile as a function of time on the breached skin surface during therapy.

In the embodiment of FIG. 3, a healthy unbroken skin temperature in the wrist region is between 30° C. and 33° C., and the temperature of the injured skin under therapy can have an initial temperature dip for a certain duration which is followed by a substantially constant temperature for another duration. Typically, the initial injury skin temperature dip is between +5° C. to +20° C. for the duration up to 10 minutes. The initial low temperature dip is such that the medical patient does not feel too cold and must have the device removed. After the initial temperature dip, the skin temperature can start to rise and attain an equilibrium within a substantially constant temperature range. The follow-on cooling temperature and its duration depend on the type of wound and the condition of the medical patient, either in a sedated or in a conscious state. A typical temperature in the follow-on phase is between +10° C. and +25° C. for a duration of between 5 minutes to 20 hours. In case of medical need, a new device may replace a prior device after the prior device has reached ambient temperature. The total length of time that the device is applied to the patient can typically be 24 hours or less for an overnight in-patient. Depending on the hospital protocol and the medical need of the patient, the device can also be applied on a medical patient for a longer period of time.

The coolant container 400 in FIG. 2 can be made of a metal material, a polymeric material, either a plastic or an elastomer, or a combination of different materials. The material of coolant container 400 can be selected from various classes of metals or metal alloys such as steel, copper, brass, titanium, titanium alloy, aluminum, iron and the like. The material of the coolant container 400 can be selected from various classes of plastics or elastomers including, without limitation, polycarbonate, polystyrene, low-density polyethylene, high density polyethylene, polypropylene, ABS, nylon, polyurethane, polyvinylchloride, polyvinyl alcohol, terephthalate, polyethylene glycol, neoprene, poly-vinyl-pyrrolidone and methacrylates, ethylene vinyl acetate, polytetrafluoroethylene, expanded polytetrafluoroethylene, fluorinated polymer, fluorinated elastomer, polyolefin, silicon-containing polymer, polyacrylamide, polycrylonitrile-polyacrylamide, polyester, polysilicone, a mixture of the aforementioned biocompatible materials, or the like. The flexible thin film encapsulating the coolant 215 is resistant to chemical and resistant to corrosion and can be selected from various classes of polymers such as polyethylene, polypropylene, polyurethane, silicone or the like.

Alternatively, the material of all components in coolant container 400 is made of transparent or semi-transparent material to enable medical personnel to conduct visual inspection of the wound site without disturbing the wound and the device.

Figure 4:
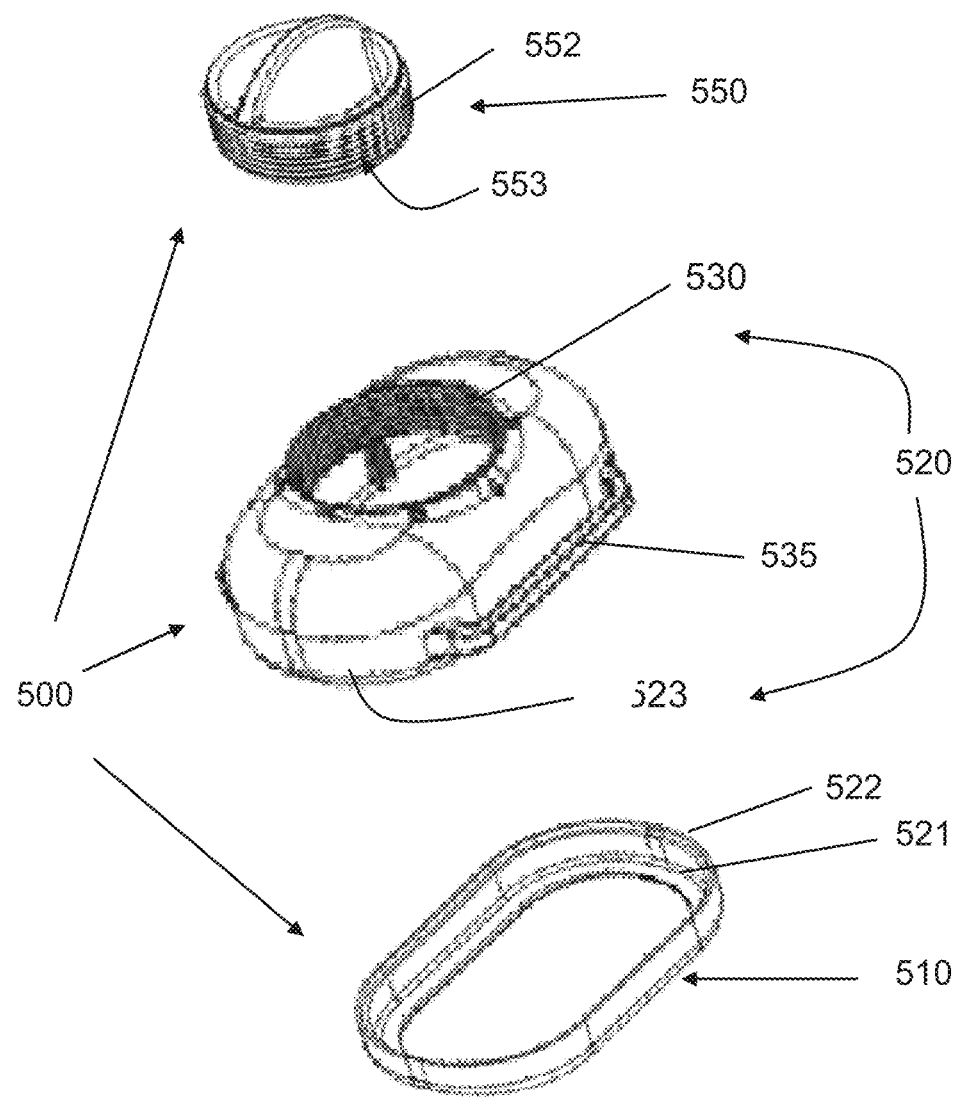
FIG. 4 is an exemplary embodiment of an exploded view of the components of the vertical displacement casing for the coolant container providing the coolant container with reversible, incremental and independent vertical displacement.

FIG. 4 is an embodiment of the exploded view of various components of the vertical displacement casing 500 where the vertical displacement casing comprises 3 components: a coolant container ring 510, a housing 520 and a presser 550. The bottom circumference of housing 520 fits snuggly to the upper circumference 411 of the coolant reservoir 410 in FIG. 2. The container ring 510 provides the support for the lower portion 412 of the coolant reservoir 410 in FIG. 2 to perform vertical displacement independent of the container ring 510 and the housing 520. The presser 550 acts to affect and control the vertical displacement of the coolant container 400 in a reversible and incremental manner. The container ring 510 has a stop 521 to allow the lower portion 412 of the coolant reservoir 410 to protrude out of the container ring 510 to a certain pre-determined total height, that is, the total vertical displacement. The presser 550 is inserted into the presser cavity 530 of the housing 520 to affect the vertical displacement and the entire unit, 550 and 520, is then snuggly fitted to the container ring 510 by mating between 522 and 523 to become one unit. In one embodiment, the presser 550 has a presser height 552 and a flat bottom 553. The presser height 552 corresponds to the height of the lower portion 412 of the coolant reservoir 410 in FIG. 2 and together determines the amount of total vertical displacement. The flat bottom 553 of the presser 550 is in direct contact of the flat top surface of the cap 420 in the coolant container 400. The adjustment of the presser, for example without limitation, by turning the thread in the presser 550, clockwise or counterclockwise, thus either pushes down or raises the coolant container 400 relative to the wound. The vertical movement of coolant container 400 in turn provides a compressive force to the wound, or releases the compressive force from the wound. Handle 535 is a mechanism to hold lateral stabilization component and two handles are present on opposite sides of 520.

Similarly, the material for all components in vertical displacement casing 500 can be made of a metal material, a polymer material, either a plastic or an elastomer, or the combination of different materials. The material of vertical displacement casing 500 can be selected from various classes of metals or metal alloys such as steel, copper, brass, titanium, titanium alloy, aluminum, iron and the like. The material of the vertical displacement casing 500 can be selected from various classes of plastics or elastomers including, without limitation, polycarbonate, polystyrene, low-density polyethylene, high density polyethylene, polypropylene, ABS, nylon, polyurethane, polyvinylchloride, polyvinyl alcohol, terephthalate, polyethylene glycol, neoprene, poly-vinyl-pyrrolidone and methacrylates, ethylene vinyl acetate, polytetrafluoroethylene, expanded polytetrafluoroethylene, fluorinated polymer, fluorinated elastomer, polyolefin, silicon-containing polymer, polyacrylamide, polycrylonitrile-polyacrylamide, polyester, polysilicone, a mixture of the aforementioned biocompatible materials, or the like. The material for the vertical displacement casing 500 is transparent or semi-transparent to enable medical personnel to conduct a visual inspection of the wound site without disturbing the wound, or without removing the device. The thin film encapsulating the coolant is flexible and resistant to chemical and resistant to corrosion and can be selected from various classes of polymers such as polyethylene, polypropylene, polyurethane, silicone or the like.

Figure 5:
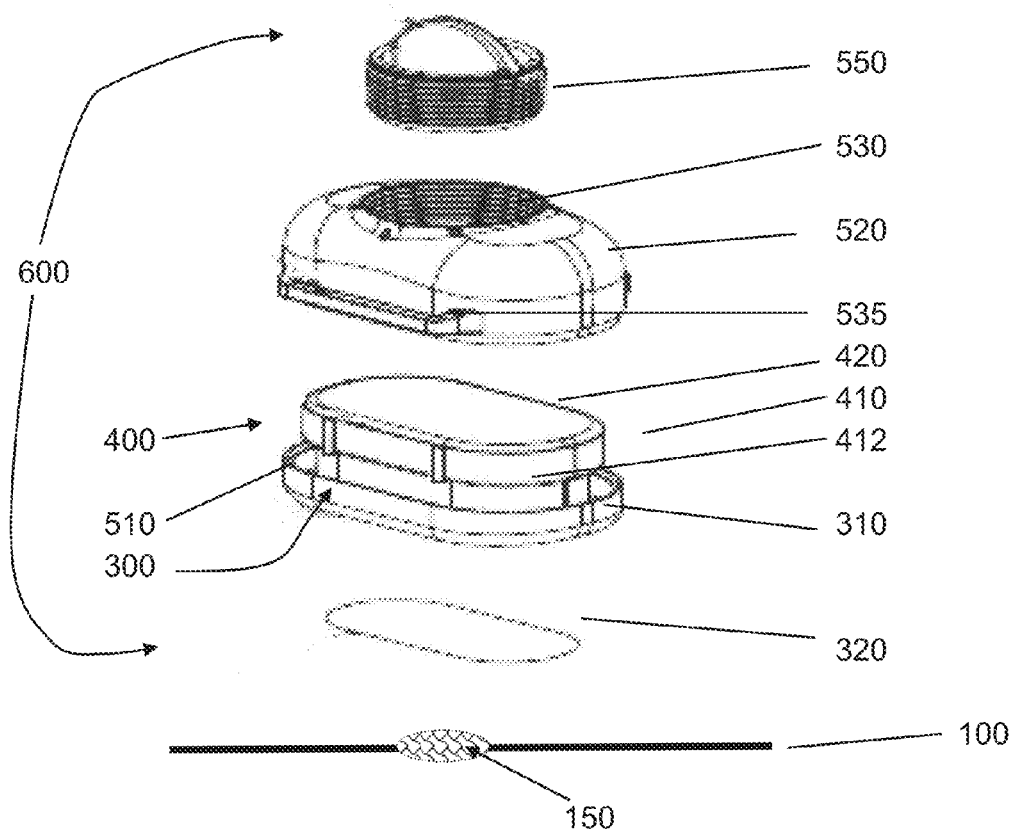
FIG. 5 is an exemplary embodiment of an exploded view of all components of CCC and CCS as applied to the breached skin surface of the wound.

FIG. 5 represents an embodiment of an exploded view of all components in the delivery member 600 minus the lateral stabilization component. In other words, FIG. 5 depicts the components to be assembled in the cooling compressive surface (CCS) and the cooling compressive compartment (CCC). The exploded view in FIG. 5 shows (A) the cooling compressive surface (CCS) 300, 310 and 320, and (B) the cooling compressive compartment (CCC) comprising the coolant container (reservoir 410 and its cap 420) and (C) the vertical displacement casing (ring 510, housing 520 and presser 550).

During operation, the operator will adjust the presser 550 and the movement of the presser 550 will affect the coolant container 400 to move up and down causing vertical displacement. In this operation, the bottom part of the reservoir 412 protrudes out of the ring 510 and comes in contact with the injury site. The total vertical displacement of the coolant container is between 0.2 mm and 3.0 cm, and the greater the vertical displacement, the greater the compressive pressure.

The vertical displacement of the CCC in this invention imparts only a force in a substantially vertical direction to the wound site, without imparting forces in another manner such as pulling or twisting to cause further injury to the wound. The vertical displacement can be finely tuned to as small an increment as possible, i.e. 0.05 mm, to accommodate a particular medical need for a particular injury or a particular anatomy. The adjustment of vertical displacement, thus the adjustment of the compressive pressure, can be done in a precise, reversible and incremental manner to minimize irritation or agitation to the wound and promote hemostasis and wound healing.

Figure 6:
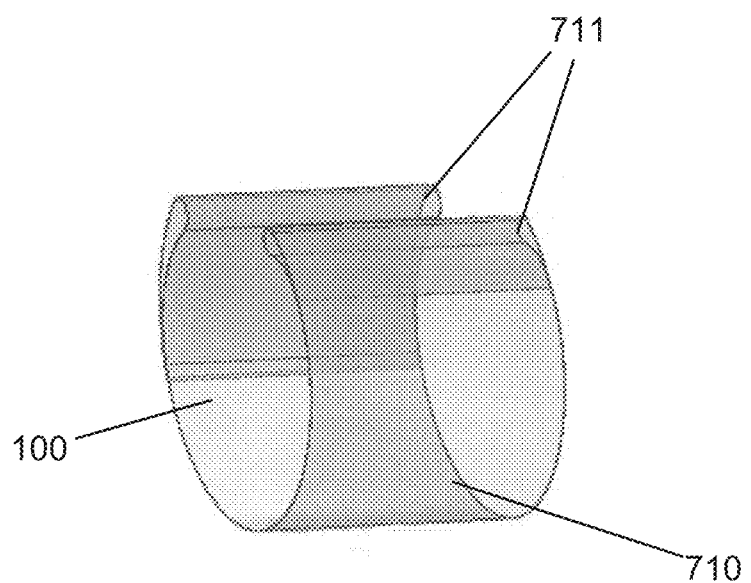
FIG. 6 is an exemplary embodiment of the lateral stabilization component.

FIG. 6 shows one exemplary embodiment of the lateral stabilization component. FIG. 6 can be a strap 710 strapping around the back side of the radial percutaneous access site 100 with two ends 711 of the strap engaged to the two handles 535 on both sides of housing 520 in FIG. 4. The strap 710 is independent of, and unaffected by, the vertical displacement 412 in the coolant container 400.

FIG. 7 shows another exemplary embodiment of the lateral stabilization component stabilizing the anatomical structures in the vicinity of the breached injured skin surface 150. Even though the unbroken skin 100 is depicted as a cylindrical structure, the unbroken skin 100 can be any part of the anatomy with any structural shape. FIG. 7A depicts the stabilization component 720 prior to use. The lateral stabilization component can be shaped such that the securing mechanism 721 surrounds only one part of the injured anatomical structure and its surroundings. The lateral stabilization component 720 has an opening 722 and is secured with a Velcro® or another adhesive tape 723. The two attachment ends can be fastened together with other connectors or securing mechanisms, for example, without limitation, the opening 722 can be a buckle, a clasp, a hook, a loop, Velcro®, a adhesive tape, a D-ring, or the like.

In FIG. 7A, the mate of Velcro is also placed on the other side of 721 and not shown in this figure. FIG. 7B depicts the lateral stabilization component after application 730. To secure, an operator would insert one end of the pre-Velcro® securing mechanism 723 through the opening 722 and, after insertion, both ends are pulled with even pressure in opposite directions 740 until appropriate fit. After fitting is secured, the operator then mates two Velcro® parts to secure the structure. By pulling 740 to secure the stabilization component, the wound encountered a lateral compressive pressure as depicted in 750, thus returning the injury flap to its anatomical position. The lateral stabilization component 720 is independent, does not affect and is not affected by the cooling compressive component 600 and the CCS 300 applied at the injury site 150.

The lateral stabilization component can be made of a polymeric material or a combination of two or several polymeric materials. The polymer can be natural-occurring or synthetic. Alternatively, the polymer can be a natural fabric, or a synthetic fabric or a non-woven. The natural fabric can be, for example without limitation, cotton, silk or wool. The synthetic fabric, woven or non-woven, can be made of, for example without limitation, polyethylene, polypropylene, ethylene propylene copolymer, polyester, nylon, polycrylonitrile, polypropylene, polyacrylonitril-polyacrylamide, polyacrylic, polyamide, and the like. Alternatively, the lateral stabilization component polymer can be stretchable or non-stretchable. The polymeric fabric can be of different deniers.

FIG. 8 is an exemplary embodiment of the side view of a hemostasis and wound healing device 800 representing a fully assembled delivery member, without the lateral stabilization component, for percutaneous radial access site. FIGS. 8A and 8B are shown without a lateral stabilization component while FIG. 8C a computer-rendered entire assembly including a lateral stabilization component on the wrist of a model. In FIG. 8A, the presser 550 in a form of a thread screw in the vertical displacement casing 500 is in the raised and resting pre-application position and the lower portion 412 of the coolant reservoir 410 is at a raised position 810 and not visible. In FIG. 8B, the presser 550 is fully turned down and depressed and the lower portion 412 of the coolant reservoir 410 is lowered by a certain vertical displacement 820 and visible in the side view. Notice that the coolant reservoir 410 is depressed and displaced from the original configuration relative to the casing 500 and independent of the casing 500. In both FIGS. 8A and 8B, the cooling compressive surface 300 and its components 310 and 320 are not visible. FIG. 8C depicts a computer-rendered image of a radial cooling compressive device applied to the percutaneous radial access site of a model hand after a medical procedure.

The foregoing has described the principles, embodiments, and modes of operation of the present invention. However, the invention should not be construed as being limited to the particular embodiments described above, as they should be regarded as being illustrative and not as restrictive. Modifications and variations of the present invention are possible in light of the above teachings. It is therefore to be understood that the invention may be practiced otherwise than as specifically described herein. It should be appreciated that variations may be made in those embodiments by those skilled in the art without departing from the scope of the present invention.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A topical hemostasis and wound healing device for affecting a hemostasis phase and a wound healing phase of a vascular wound or an acute surgical wound in a medical patient, comprising:

a delivery member comprising a cooling compressive surface, a cooling compressive compartment and a lateral stabilization component configured to deliver cooling and compression to the wound, and a therapeutic agent, wherein said delivery member is configured to the vascular wound or acute surgical wound and said device is anatomically conforming and affects said hemostasis phase and said wound healing phase;

wherein the cooling compressive compartment comprises a coolant container and a vertical displacement casing, the coolant container being displaced in a substantially vertical direction towards or away from the wound in a precise, reversible, and incremental manner to affect a compression pressure to resist blood outward flow during said hemostasis phase and said wound healing phase; and wherein vertical displacement of the coolant container is independent of the casing by protruding out of the casing between 0.2 mm and 3.0 cm affecting a compressive pressure to the wound of between 0.2 psi and 20 psi.

2. The device according to claim 1, wherein the cooling compressive surface is configured to resist blood outward flow and conform to the vascular wound.

3. The device according to claim 2, wherein the cooling compressive surface comprises one or more than one component and at least one component has an elastic tensile modulus between 50 kPa and 100 MPa.

4. The device according to claim 2, wherein at least one component of the cooling compressive surface is a thermally conductive polymeric material.

5. The device according to claim 4, wherein the thermal conductivity is between 0.15 W/(m-K) and 100 W/(m-K).

6. The device according to claim 1 wherein the coolant container contains a coolant.

7. The device according to claim 6, wherein the coolant delivers and transports cooling temperature to said wound by a passive means or by an active means.

8. The device according to claim 6, wherein the coolant is water or water containing at least one electrolyte or water containing at least one polymeric material.

9. The device according to claim 6, wherein the coolant is a phase change material.

10. The device according to claim 9, wherein the phase change material is selected from the group consisting of bio-based fat, fatty acid, ester, oil, petroleum-based product, synthetic alkane, ester, mineral oil, paraffin, other organic derivative, and any combination thereof.

11. The device according to claim 10, wherein the phase change material has a melting temperature between −15° C. to +25° C.

12. The device according to claim 1, wherein the lateral stabilization component secures the cooling compressive surface and the cooling compressive compartment to said wound.

13. The device according to claim 12, wherein the lateral stabilization component is configured to conform to the anatomy of said wound and vicinity of said wound.

14. The device according to claim 1, wherein the cooling compressive surface has a surface area equal to, or substantially larger than, a breached skin injury and the surface area is of uniform temperature or has two or more different temperature zones.

15. The device according to claim 1, wherein the device produces an initial temperature of skin surrounding said wound of between +5° C. to +20° C. for up to 10 minutes and a follow-on temperature between +10° C. to +25° C. of between 5 minutes to 20 hours.

16. The device of claim 1 wherein said therapeutic agent is selected from the group consisting of cellular proliferation inhibitor, smooth muscle inhibitor, inhibitor of vascular cell growth, anti-proliferative agent, neural blockade agent, anti-inflammatory agent, antibiotic, anesthetic agent, analgesic agent, pain killing agent, neuroprotectant, vasoconstriction agent, sclerosant agent, gene, DNA, RNA, polypeptide, protein, blood coagulation agent, platelet agent, blood-clotting agent, hemostasis agent, wound healing agent, and any combination thereof.

17. A method of affecting a hemostasis phase and wound healing phase in a medical patient thereof comprising: placing the device of claim 1 on a surface of skin surrounding a wound; applying manual pressure by manually holding down the device on a wound site to prevent blood outward flow to anatomical surrounding of the wound, adjusting a presser in the vertical displacement casing to affect vertical displacement of the coolant container containing coolant towards the wound, stopping the presser to advance further vertical displacement upon visual verification of no blood oozing out on the breached skin surface, allowing for delivery or transport of a cooling temperature to the wound, reversing the vertical displacement upon wound healing, and removing said device at the completion of said hemostasis and wound healing.

* * * * *